US005881720A

United States Patent [19]

Vinogradov et al.

[11] Patent Number: 5,881,720
[45] Date of Patent: Mar. 16, 1999

[54] METHOD OF DELIVERING HALOTHERAPY

[75] Inventors: Valentin Vinogradov, Moscow, Russian Federation; Robert S. Dirksing, Cincinnati, Ohio

[73] Assignee: The Procter & Gamble Company, Cincinnati, Ohio

[21] Appl. No.: 841,132

[22] Filed: Apr. 29, 1997

[51] Int. Cl.[6] ........................ A61M 15/00; A61M 16/00; B05D 7/14; B65D 83/06

[52] U.S. Cl. ............................... 128/203.15; 178/700.14; 178/703.12

[58] Field of Search ........................ 128/200.14, 203.12, 128/203.15

[56] References Cited

U.S. PATENT DOCUMENTS

| | | | |
|---|---|---|---|
| 4,933,169 | 6/1990 | Shanbrom | 424/46 |
| 5,215,221 | 6/1993 | Dirksing | 222/94 |
| 5,263,475 | 11/1993 | Altermatt et al. | 128/203 |
| 5,283,268 | 2/1994 | Johnson et al. | 514/357 |
| 5,510,339 | 4/1996 | Gleich et al. | 514/171 |
| 5,533,505 | 7/1996 | Kallstrand et al. | 128/203 |
| 5,655,523 | 8/1997 | Hodson et al. | 128/203.12 |
| 5,656,256 | 8/1997 | Boucher et al. | 424/45 |
| 5,676,643 | 10/1997 | Cann et al. | 604/1 |
| 5,681,555 | 10/1997 | Gleich | 424/78.05 |
| 5,817,028 | 10/1998 | Anderson | 600/529 |

*Primary Examiner*—John G. Weiss
*Assistant Examiner*—Joseph F. Weiss, Jr.
*Attorney, Agent, or Firm*—Jack L. Oney Jr.

[57] ABSTRACT

A method of providing halotherapy to the upper portion of the lower respiratory tract includes the steps of operating a dispenser and inhaling. The dispenser contains a dry sodium chloride powder. The user operates the dispenser to release a dosage of the powder for inhalation when the dispenser is aimed into the user's mouth. The user then inhales the dosage of powder through the mouth. Because the powder has a particle size range enabling the powder to target the upper portion of the lower respiratory tract without entering the user's lungs, the dosage of the dry powder provides a concentration at the upper portion sufficient to provide effective halotherapy. The preferred particle size range is from about 5 microns to about 20 microns. The preferred dosage is about 3 milligrams of powder.

16 Claims, 2 Drawing Sheets

METHOD OF DELIVERING HALOTHERAPY

FIELD OF THE INVENTION

The present invention relates to a method of delivering a fine powder to the upper portion of a person's lower respiratory tract to provide symptomatic treatment of ailments due to the common cold and respiratory discomfort due to allergies, and to provide general oral and respiratory hygiene. More particularly, the present invention relates to a method for delivering a predetermined dose quantity of dry powdered sodium chloride.

BACKGROUND OF THE INVENTION

Treatment of respiratory diseases by inhalation of fine rock salt particles (halotherapy) in salt caves or salt mines has been practiced for centuries in places such as Eastern Europe. The efficacy is associated with the unique micro climate within the salt caves and mines. The main curative factor is an atmosphere saturated with dry sodium chloride aerosol with particles of 2 to 5 microns in size. The salt aerosol is formed by the convective diffusion of the fine salt particles from the salt walls. Halotherapy has been recognized as a highly effective drug-free treatment for patients with various forms of chronic nonspecific pulmonary diseases. In a typically treatment, a patient will reside in the salt caves for up to twelve hours per day, breathing in the fine salt powder. In areas where salt mines are not available, special rooms have been constructed in which the environmental conditions of the salt mines are artificially reproduced. The patient resides in the halotherapy rooms in like manner as for the salt caves or mines.

Recent studies have indicated that much shorter exposures to aerosolized dry powder salt can provides relief of symptoms of common colds, e.g., sore throat, cough, headache, etc. These studies were conducted with a bench top laboratory system having a means for aerosolizing a quantity of fine powdered salt located within an enclosed chamber. One wall of the chamber included an opening at which a patient's face was positioned so that the atmosphere of aerosolized dry powder salt was available for inhalation. The bench top system provided the respiratory benefit without requiring the patient to be physically located within the chamber. While the patient was not inconvenienced by having to remain in a cave for an extended period, the patient was effectively restricted by the laboratory system. A portable powder delivery system is therefore needed for commercial usefulness of halotherapy.

Aerosolized liquid saline sprays, that are delivered by rather complex medical hardware, are often used in intensive care facilities. These sprays are commonly used to increase mucociliary clearance. However, liquid saline sprays are not well suited in size and cost to provide relief of symptoms to the common cold sufferer because the salt in a liquid saline solution is highly diluted. Thus, liquid saline sprays do not deliver the much higher concentrations of salt to the airways of the lower respiratory tract possible with dry salt powder inhalation.

It has also been long recognized that gargling with a salt solution provides relief from some of the symptoms of colds, primarily sore throat. In fact some studies have indicated that the relief afforded by a salt gargle matches the performance of some over-the-counter sore throat sprays and lozenges. However beneficial salt water gargling may be, it is usually inconvenient to avail oneself of such a remedy.

There are available dry powder inhalers (DPI) which are intended to deliver drugs to the lower portion of the lower respiratory tract, primarily to the lungs, for relief of ailments of the lungs, such as asthma, or to provide systemic drug delivery through the very large surface and thin membranes of the lungs. Accordingly, the drug particle size and properties are optimized for delivery to the lower portion of the lower respiratory tract. For example, particle sizes in the range of 1 microns to 5 microns are useful for powder delivery to the lungs.

Halotherapy for treatment of cold symptoms is directed to the topical application of salt particles at the upper portion of the lower respiratory tract. A portable dry powder delivery system, matched to the desired distribution of the salt particles, is needed for a convenient means for providing drug free cold symptom relief. Furthermore, convenient topical application of salt powder to the upper portion of the lower respiratory tract can provide relief from everyday discomfort due to such problems as allergies, post nasal drip, etc. Moreover, other ingredients may be added to a salt powder, such as menthol or breath fresheners, that could provide an aid in routine throat clearing and freshening of breath.

It is therefore an object of the present invention to provide a method which can deliver dose quantities of dry fine powdered sodium chloride for topical treatment of the upper portion of the lower respiratory tract from a simple and inexpensive portable delivery device.

SUMMARY OF THE INVENTION

In one aspect of the present invention, a method of providing halotherapy to the upper portion of the lower respiratory tract comprises the steps of operating a dispenser and inhaling. The dispenser contains a dry sodium chloride powder. The user operates the dispenser to release a dosage of the powder for inhalation when the dispenser is aimed into the user's mouth. The user inhales the dosage of powder through the mouth. Because the powder has a particle size range enabling the powder to target the upper portion of the lower respiratory tract without entering the user's lungs, the dosage of the dry powder provides a concentration at the upper portion sufficient to provide effective halotherapy. The preferred particle size range is from about 5 microns to about 20 microns. The preferred dosage is about 3 milligrams of powder.

The dry sodium chloride powder preferably includes excipients, such as lactose, to prevent agglomeration of the powder. The dry sodium chloride powder may also include ingredients to enhance halotherapy, such as ascorbic acid, menthol, mint flavors, citrus flavors, breath fresheners, and a combination thereof.

The dispenser is preferably selected from a group consisting of single dose sprayers which propel powder when actuated, multiple dose sprayers which propel powder when actuated, single dose inhalers which enable powder to enter a user's breath during inhalation, and multiple dose inhalers which enable powder to enter a user's breath during inhalation.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawing in which:

DETAILED DESCRIPTION OF THE INVENTION

Figure 1:
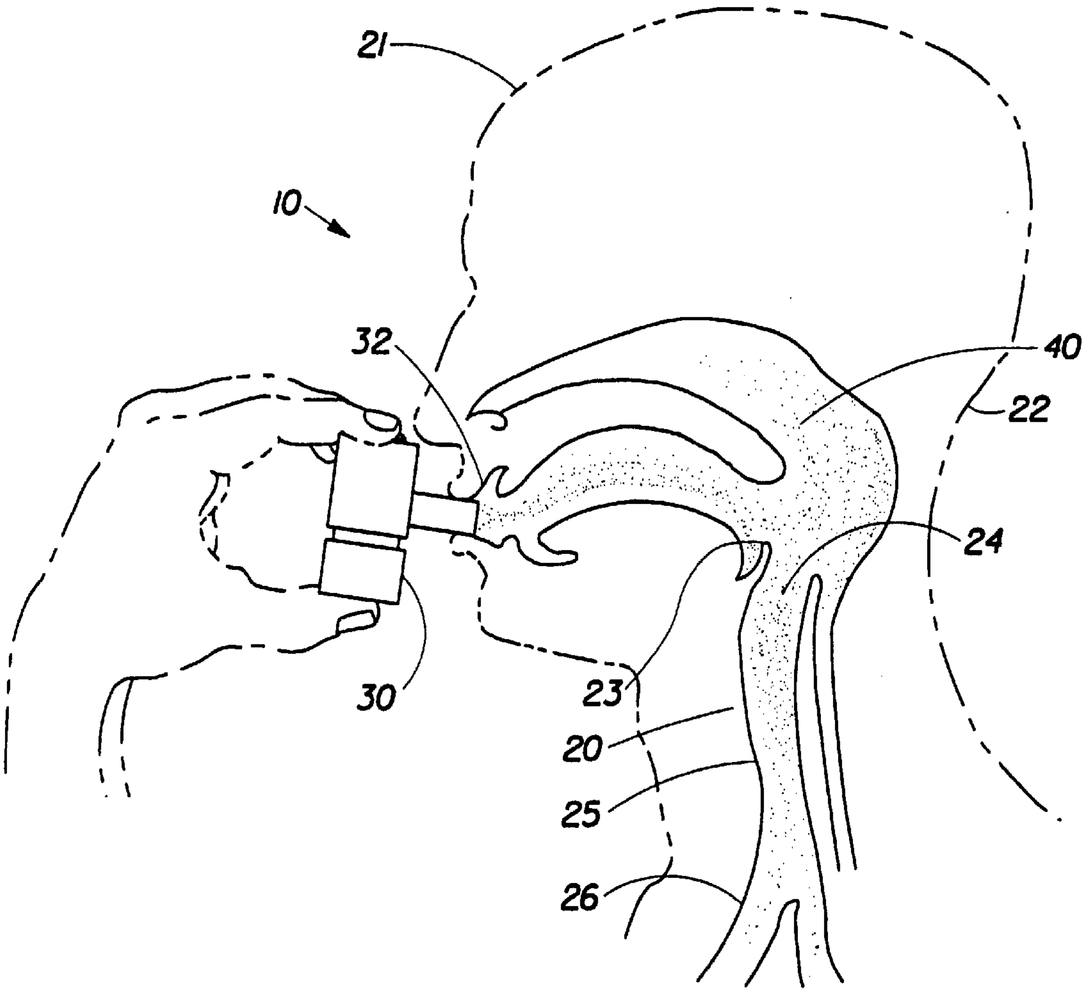
FIG. 1 is side elevation schematic view of the method for delivering halotherapy of the present invention, showing a person holding a dry powder inhaler at their mouth and the flow of powder from the inhaler to the intended internal target area.

Referring now to the drawings, and more particularly to FIG. 1, there is shown a preferred method of delivering halotherapy of the present invention, which is generally indicated as 10. A halotherapy patient or user 21 has a lower respiratory tract 20, which has an upper portion that includes a pharynx 22, an epiglotis 23, a larynx 24, a trachea 25, and a bronchial tube 26. Method 10 includes use of a dry powder inhaler 30 by user 21. Inhaler 30 is suitable for delivering a predetermined dose quantity of a dry powdered sodium chloride 40 having a particle size distribution in the range from about 5 microns to about 50 microns. Dry powdered sodium chloride 40 is delivered into a breath air stream as user 21 inhales through mouth 32 to topically administer dry powdered sodium chloride 40 to the surfaces of the upper portion of lower respiratory tract 20.

In a particularly preferred embodiment of the present invention, a suitable multiple use inhaler having a bulk reservoir of powdered sodium chloride for multiple dosing, a means for releasing a predetermined metered dose of powdered sodium chloride, and a means for enabling the predetermined metered dose of powdered sodium chloride to mix with a user's breath in response to inhalation by the user, may be used to administer halotherapy to the upper portion of the lower respiratory tract, in particular, the larynx, trachea, bronchi, and upper lung. Such a multiple use inhaler is disclosed in U.S. Pat. No. 5,263,475 issued to Altermatt et al. on Nov. 23, 1993. This inhaler meters a predetermined quantity of solids from a storage chamber into an air channel wherein the particles are mixed with an air stream generated by the inhaled breath of the user. The air stream transports the solids through the oral cavity and into the respiratory tract. In the particularly preferred embodiment for providing halotherapy of the present invention, a supply of fine powdered sodium chloride is provided in the bulk reservoir.

Excipients, such as lactose, may be added to sodium chloride particles to prevent agglomeration of the particles or as additional bulk to aid in precise metering of small quantities of the fine powdered sodium chloride. Other minor ingredients may be added such as ascorbic acid (vitamin C), menthol, breath fresheners or the like to enhance the pleasantness and efficacy of the salt therapy.

In another preferred embodiment of the present invention, the user may use a suitable single use inhaler having a single predetermined dose of fine powdered sodium chloride and means for delivering the predetermined metered dose of powdered sodium chloride in response to the inhalation. Such a single use dispenser is disclosed in U.S. Pat. No. 5,533,505 issued to Kallstrand et al. on Jul. 9, 1996. This dispenser presents a predetermined quantity of powdered product in a compartment which is mixed in an air stream generated by the inhaled breath of the user. The air stream transports the powdered product through the oral cavity and into respiratory tract.

Figure 2:
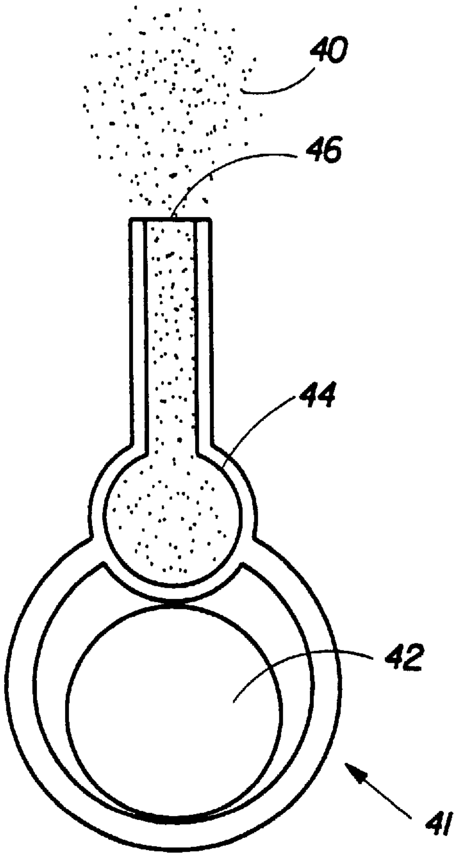
FIG. 2 is a top plan view of a prior art device intended for propelling a single dose of dry powder therefrom.
Figure 3:
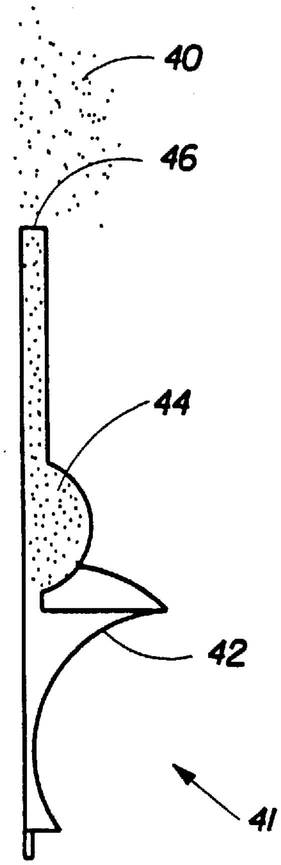
FIG. 3 is a side elevation view thereof, showing a hemispherical air-filled bulb being deformed in order to propel powder from a downstream chamber outwardly through a discharge orifice.

In yet another preferred embodiment of the present invention, a suitable single use dispenser has a single predetermined dose of powdered sodium chloride and means for propelling the predetermined dose of powdered sodium chloride into the inhaled breath of the user. Such a single use dispenser is disclosed in commonly owned U.S. Pat. No. 5,215,221 issued to Dirksing on Jun. 1, 1993, and is hereby incorporated herein by reference. FIGS. 2 and 3 show this prior art dispenser, generally indicated as 41. Dispenser 41 has a hemispherical air-filled bulb 42, a powder reservoir 44, and a discharge orifice 46. When orifice 46 is aimed into the user's mouth and bulb 42 is pressed between thumb and finger by the user, sodium chloride powder 40 is propelled through orifice 46 from reservoir 44 by the burst of air generated by deforming bulb 42. The user takes a breath through mouth 32 while rapidly pressing bulb 42, thereby mixing powder 40 with the inhaled air. Inhaled air is directed to the user's lower respiratory tract by the reduced air pressure generated by the lungs; however, powdered sodium chloride having a particle size range from about 5 microns to about 20 microns has sufficient volume and mass to be deposited from the inspired air onto the mucosal surfaces of the upper portion of the lower respiratory tract without being carried into the lungs. Particle sizes lower than 5 microns can typically be expected to be carried into the lungs, beyond the preferred topical treatment zone. Particle sizes above 50 microns can be expected to be so large that inhalation air velocity may be insufficient to transport them beyond the oral cavity.

In a particularly preferred embodiment, sodium chloride particle size ranges from 5 microns to 20 microns, and a predetermined dose is 3 milligrams of powder. Such a dose provides a light coating of fine powdered sodium chloride onto the mucosal surfaces of the upper portion of the lower respiratory tract to relive soreness and enhance expectoration. Actual dosage may vary by individual user but doses above 5 milligrams may induce coughing while doses below 1 milligram may not provide sufficient coating.

Excipients may be added to sodium chloride powder to improve dispensing properties. An example is lactose. Lactose is typically added for this purpose in the range of 2 to 5 percent. Other ingredients may be added to the mixture, such as potassium chloride, ascorbic acid, menthol, mint flavors, citrus flavors, breath fresheners, and a combination thereof These ingredients are added such that they typically have a proportion by weight less than about 10 percent and may be added to enhance expectoration.

While particular embodiments of the present invention have been illustrated and described, it will be obvious to those skilled in the art that various changes and modifications may be made without departing from the spirit and scope of the invention, and it is intended to cover in the appended claims all such modification that are within the scope of the invention.

What is claimed is:

1. A method of providing halotherapy to an upper portion of a lower respiratory tract of a user, said method comprising the steps of:

a) operating a dispenser containing dry sodium chloride powder, said dispenser releasing a dosage of said powder for inhalation when aimed into a user's mouth;

b) directing said dosage of said powder, said powder having a particle size range from about 5 microns to about 20 microns, said powder particle size range being not less than 5 microns, said powder particle size range enabling said powder to target the upper portion of the lower respiratory tract of the user without entering the user's lungs when inhaled by the user, said dosage of said dry powder providing a concentration at the upper portion of the lower respiratory tract of the user sufficient to provide effective halotherapy.

2. The method of claim 1 wherein said dry sodium chloride powder includes excipients to prevent agglomeration of said powder.

3. The method of claim 1 wherein said dry sodium chloride powder includes ingredients to enhance halotherapy, said ingredients being selected from a group consisting of potassium chloride, ascorbic acid, menthol, mint flavors, citrus flavors, breath fresheners, and a combination thereof.

4. The method of claim 1 wherein said dosage comprises about 3 milligrams of powder.

5. The method of claim 1 wherein said dispenser is selected from a group consisting of single dose sprayers which propel powder when actuated, multiple dose sprayers which propel powder when actuated, single dose inhalers which enable powder to enter a user's breath during inhalation, and multiple dose inhalers which enable powder to enter a user's breath during inhalation.

6. The method of claim 1 wherein said powder has a particle size range from about 5 microns to about 50 microns.

7. A method of providing halotherapy to an upper portion of a lower respiratory tract of a user, said method comprising the steps of:

a) operating a dispenser containing dry sodium chloride powder having a particle size range from about 5 microns to about 20 microns, said powder particle size range being not less than 5 microns, said dispenser releasing a dosage of said powder of about 3 milligrams for inhalation when aimed into a user's mouth;

b) directing said dosage of said powder, said powder having a particle size range enabling said powder to target the upper portion of the lower respiratory tract of the user without entering the user's lungs when inhaled by the user, said dosage of said dry powder providing a concentration at the upper portion of the lower respiratory tract of the user sufficient to provide effective halotherapy.

8. The method of claim 7 wherein said dry sodium chloride powder includes excipients to prevent agglomeration of said powder.

9. The method of claim 7 wherein said dry sodium chloride powder includes ingredients to enhance halotherapy, said ingredients being selected from a group consisting of potassium chloride, ascorbic acid, menthol, mint flavors, citrus flavors, breath fresheners, and a combination thereof.

10. The method of claim 7 wherein said dispenser is selected from a group consisting of single dose sprayers which propel powder when actuated, multiple dose sprayers which propel powder when actuated, single dose inhalers which enable powder to enter a user's breath during inhalation, and multiple dose inhalers which enable powder to enter a user's breath during inhalation.

11. A delivery system for providing halotherapy to an upper portion of a user's lower respiratory tract comprising a dispenser containing dry sodium chloride powder, said dispenser releasing a dosage of said powder for inhalation when aimed into a mouth of said user and when said user simultaneously inhales said dosage of said powder through said mouth, said powder having a particle size range from about 5 microns to about 20 microns, said powder particle size range being not less than 5 microns, said powder particle range enabling said powder to target said upper portion of said user's lower respiratory tract without entering a lung of said user, said dosage of said dry powder providing a concentration at said upper portion sufficient to provide effective halotherapy.

12. The delivery system of claim 11 wherein said dry sodium chloride powder includes excipients to prevent agglomeration of said powder.

13. The delivery system of claim 11 wherein said dry sodium chloride powder includes ingredients to enhance halotherapy, said ingredients being selected from a group consisting of potassium chloride, ascorbic acid, menthol, mint flavors, citrus flavors, breath fresheners, and a combination thereof.

14. The delivery system of claim 11 wherein said dosage comprises about 3 milligrams of powder.

15. The delivery system of claim 11 wherein said dispenser is selected from a group consisting of single dose sprayers which propel powder when actuated, multiple dose sprayers which propel powder when actuated, single dose inhalers which enable powder to enter a user's breath during inhalation, and multiple dose inhalers which enable powder to enter a user's breath during inhalation.

16. The delivery system of claim 11 wherein said powder has a particle size range from about 5 microns to about 50 microns.

* * * * *